United States Patent
Mudryk et al.

(10) Patent No.: US 7,304,157 B2
(45) Date of Patent: Dec. 4, 2007

(54) EFFICIENT SYNTHESIS OF 4,5-DIHYDRO-PYRAZOLO[3,4-C]PYRID-2-ONES

(75) Inventors: Boguslaw M. Mudryk, East Windsor, NJ (US); Nicolas Cuniere, Belle Mead, NJ (US); Dau-Ming Hsieh, Edison, NJ (US); Lucius Rossano, West Windsor, NJ (US); Jing Liang, Princeton, NJ (US); Bang-Chi Chen, Plainsboro, NJ (US); Huiping Zhang, Belle Mead, NJ (US); Rulin Zhao, Pennington, NJ (US); Bei Wang, Yardley, PA (US); Adrian David, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/235,647

(22) Filed: Sep. 26, 2005

(65) Prior Publication Data

US 2006/0069119 A1    Mar. 30, 2006

Related U.S. Application Data

(60) Provisional application No. 60/613,754, filed on Sep. 28, 2004, provisional application No. 60/637,623, filed on Dec. 20, 2004.

(51) Int. Cl.
    *C07D 491/02* (2006.01)
(52) U.S. Cl. ..................................... 546/120
(58) Field of Classification Search ................ 546/120
    See application file for complete search history.

(56) References Cited

U.S. PATENT DOCUMENTS

| 6,919,451 B2 | 7/2005 | Zhou et al. |
| 6,967,208 B2 | 11/2005 | Pinto et al. |
| 2003/0181466 A1* | 9/2003 | Zhou et al. ............... 514/256 |
| 2003/0191115 A1* | 10/2003 | Pinto et al. ............... 514/224.2 |
| 2004/0220174 A1 | 11/2004 | Pinto et al. |
| 2005/0124602 A1 | 6/2005 | Pinto et al. |
| 2005/0171085 A1 | 8/2005 | Pinto et al. |
| 2005/0245566 A1 | 11/2005 | Zhou et al. |
| 2006/0069085 A1 | 3/2006 | Zhao et al. |

FOREIGN PATENT DOCUMENTS

| WO | WO 03026652 | 4/2003 |
| WO | WO03/049681 A | 6/2003 |
| WO | WO2006/036927 A1 | 4/2006 |

OTHER PUBLICATIONS

U.S. Appl. No. 11/235,510, filed Sep. 26, 2005, Shapiro et al.
U.S. Appl. No. 11/235,731, filed Sep. 26, 2005, Zhang et al.
U.S. Appl. No. 11/234,942, filed Sep. 26, 2005, Zhang et al.
U.S. Appl. No. 11/154,972, filed Jun. 16, 2005, Pinto et al.
U.S. Appl. No. 11/198,801, filed Aug. 5, 2005, Pinto et al.
Klapars et al., "A General and Efficient Copper Catalyst for the Amidation of Aryl Halides", J. Am. Chem. Soc. 2002, vol. 124, pp. 7421-7428.

* cited by examiner

*Primary Examiner*—D. Margaret Seaman
*Assistant Examiner*—Nizal S. Chandrakumar
(74) *Attorney, Agent, or Firm*—Jing G. Sun; David H. Vance

(57) ABSTRACT

A novel process and intermediates thereof for making 4,5-dihydro-pyrazolo[3,4-c]pyrid-2-ones of the type shown below from appropriate phenyl hydrazines is described.

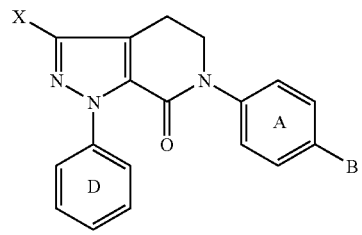

These compounds can be useful as factor Xa inhibitors.

15 Claims, No Drawings

EFFICIENT SYNTHESIS OF 4,5-DIHYDRO-PYRAZOLO[3,4-C]PYRID-2-ONES

CROSS-REFERENCE TO RELATED APPLICATIONS

This application claims a benefit of priority from U.S. Provisional Application No. 60/613,754 filed Sep. 28, 2004, and U.S. Provisional Application No. 60/637,623 filed Dec. 20, 2004, the entire disclosure of which is herein incorporated by reference.

FIELD OF THE INVENTION

The present invention relates generally to processes for the preparation of 4,5-dihydro-pyrazolo[3,4-c]pyrid-2-ones and intermediates for the synthesis of the same, such pyrazolo-pyridinones can be useful as factor Xa inhibitors.

BACKGROUND OF THE INVENTION 4,5-Dihydro-pyrazolo[3,4-c]pyrid-2-one compounds, like those described in WO 03/26652, are currently being studied as factor Xa inhibitors in clinical settings. Clinical trials and NDA submissions require practical, large-scale synthesis of the active drug and intermediates for making the active drug. Consequently, it is desirable to find new synthetic procedures for making 4,5-dihydro-pyrazolo[3,4-c]pyrid-2-ones.

SUMMARY OF THE INVENTION

Accordingly, the present invention relates to a novel process for making 4,5-dihydro-pyrazolo[3,4-c]pyrid-2-ones.

The present invention relates to novel intermediates for the syntheses of 4,5-dihydro-pyrazolo[3,4-c]pyrid-2-ones.

These and other objects, which will become apparent during the following detailed description of processes relating to compounds of the following formula.

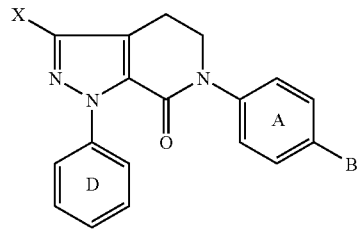

DETAILED DESCRIPTION OF THE INVENTION

Thus, in a 1$^{st}$ embodiment, the present invention provides a novel process for preparing a compound of formula IIIa:

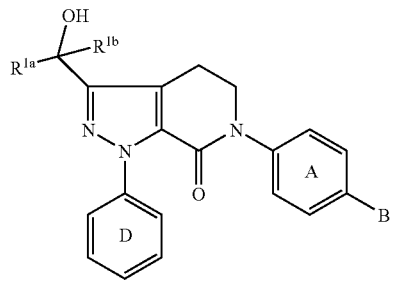

comprising:
(a) contacting a compound of formula I with a compound of formula II in the presence of a first base to form a compound of formula III;

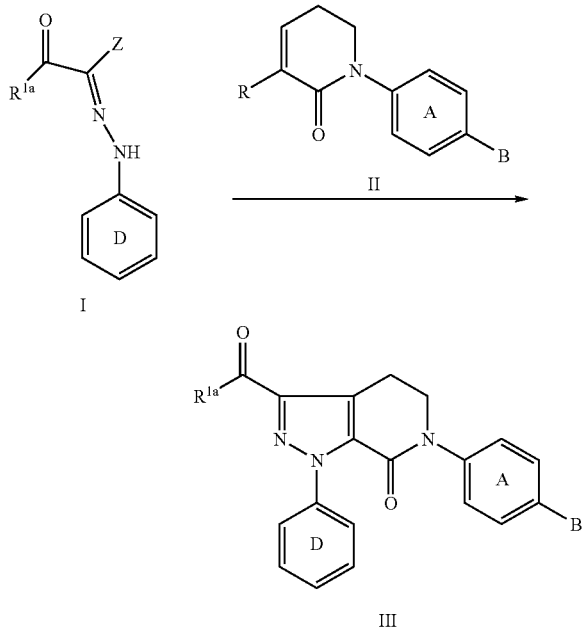

(b) contacting a compound of formula III with an $R^{1b}$-metal reagent to form a compound of formula IIIa;

wherein:
Z is selected from Cl, Br, I, $OSO_2CF_3$, $OSO_2Me$, $OSO_2Ph$, and $OSO_2Ph$-p-Me;
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;
$R^{1b}$ is $C_{1-6}$ alkyl;
R is selected from Cl, Br, I, $C_{1-6}$ alkoxy, and $NR^1R^2$;
$R^1$ and $R^2$ are independently selected from $C_{1-6}$ alkyl, cyclopropyl, cyclobutyl, cyclopentyl, cyclohexyl, phenyl, and benzyl;
alternatively, $NR^1R^2$ is a 3-8 membered ring consisting of: carbon atoms, N, and 0-1 O atoms;
ring A is substituted with 0-1 $R^4$;
B is selected from F, Cl, Br, I, $OSO_2CF_3$, $OSO_2Ph$-p-Me, and 2-oxo-pyridyl; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

In a 2$^{nd}$ embodiment, the present invention provides a novel process wherein:
Z is selected from Cl, Br, and I;
ring D is selected from 3-chlorophenyl and 4-methoxyphenyl;
$R^{1a}$ is selected from $CH_3$, $CH_2CH_3$, and $CH_2CH_2CH_3$;
$R^{1b}$ is selected from $CH_3$ and $CH_2CH_3$;
R is selected from Cl, Br, I, and $NR^1R^2$;
$NR^1R^2$ is selected from morpholino, pyrrolidino, and piperidino;
ring A is substituted with 0-1 $R^4$; and
$R^4$ is selected from H and F.

In a 3rd embodiment, the present invention provides a novel process wherein:
Z is Cl;
ring D is 4-methoxyphenyl;
$R^{1a}$ is $CH_3$;
$R^{1b}$ is $CH_3$;
R is morpholino; and
ring A is unsubstituted.

In a 4th embodiment, in reaction (a), the compound of formula I is contacted with the compound of formula II followed by the addition of the first base.

In a 5th embodiment, the first base in reaction (a) is a substituted amine base.

In a 6th embodiment, the substituted amine base is selected from: triethylamine, diisopropylethylamine, dabco, DBN, DBU, and N-methylmorpholine.

In a 7th embodiment, the substituted amine base is triethylamine.

In a 8th embodiment, in reaction (a), the contacting is performed in the presence of a first aprotic solvent.

In a 9th embodiment, the first aprotic solvent is ethyl acetate.

In a 10th embodiment, reaction (a) further comprises contacting with a first strong acid.

In an 11th embodiment, the first acid is HCl.

In a 12th embodiment, the $R^{1b}$-metal reagent is a Grignard reagent.

In a 13th embodiment, the Grignard reagent is $CH_3MgCl$.

In a 14th embodiment, in reaction (b), the contacting is performed in the presence of a second aprotic solvent.

In a 15th embodiment, the second aprotic solvent is methylene chloride.

In a 16th embodiment, the present invention provides a novel process for preparing a compound of formula IIIb:

tate-diamine ligand, and a third aprotic solvent to form a compound of formula IIb; wherein:
ring D is selected from phenyl, 2-fluorophenyl, 3-chlorophenyl, and 4-methoxyphenyl;
B is selected from F, Cl, Br, I, $OSO_2CF_3$, and $OSO_2Ph$-p-Me;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;
$R^{1b}$ is $C_{1-6}$ alkyl;
ring A is substituted with 0-1 $R^4$; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $CH(CH_3)_3$, —CN, and $CF_3$.

In a 17th embodiment, the present invention provides a novel process wherein:
ring D is selected from 3-chlorophenyl and 4-methoxyphenyl;
B is I;
$R^{1a}$ is selected from $CH_3$, $CH_2CH_3$, and $CH_2CH_2CH_3$;
$R^{1b}$ is selected from $CH_3$ and $CH_2CH_3$;
ring A is substituted with 0-1 $R^4$; and
$R^4$ is selected from H and F.

In an 18th embodiment, the present invention provides a novel process, wherein:
ring D is 4-methoxyphenyl;
B is I;
$R^{1a}$ is $CH_3$;
$R^{1b}$ is $CH_3$; and
ring A is unsubstituted.

In a 19th embodiment, in reaction (c) the catalyst is a Cu(I) salt or a Pd(II) salt and the ligand is a phenanthroline.

In a 20th embodiment, in reaction (c) the catalyst is selected from CuI, CuCl, CuBr, and CuOTf.

In a 21st embodiment, in reaction (c), the catalyst is CuI and the ligand is 1,10-phenanthroline.

In a 22nd embodiment, in reaction (c), the third aprotic solvent is selected from DMSO, toluene, N-methylpyrrolidinone, DMAC, and DMF.

In a 23rd embodiment, in reaction (c), the third aprotic solvent is DMF.

In a 24th embodiment, the present invention provides a novel process for preparing a compound of formula IIIc:

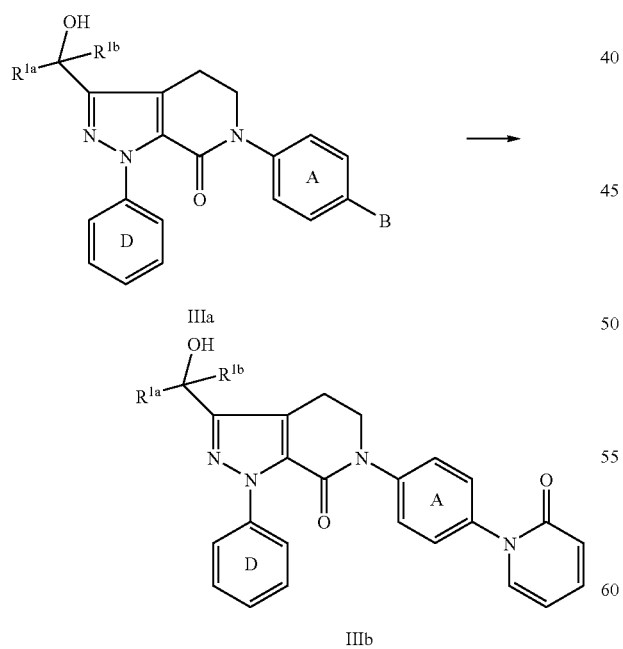

IIIa

IIIb

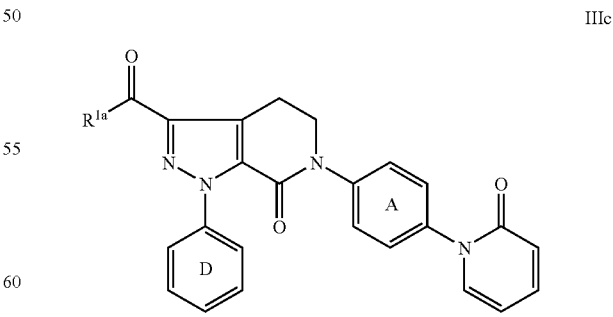

IIIc comprising:
(c) contacting the compound of formula IIIa with 2-hydroxy-pyridine in the presence of a catalyst, a bidencomprising:
(d) contacting the compound of formula IIa with 2-hydroxy-pyridine in the presence of a catalyst and a fourth aprotic solvent to form a compound of formula IIb;

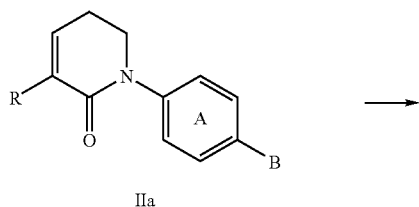

IIa

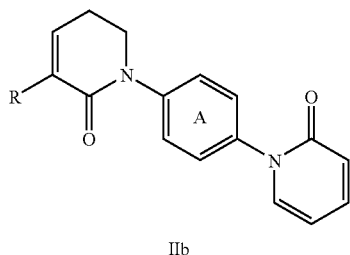

IIb (e) contacting a compound of formula I with a compound of formula IIb in the presence of a second base to form a compound of formula IIIc;

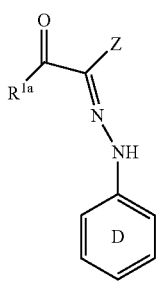

I wherein:
Z is selected from Cl, Br, I, $OSO_2CF_3$, $OSO_2Me$, $OSO_2Ph$, and $OSO_2Ph$-p-Me;
ring D is selected from phenyl, 2-fluorophenyl, 3-chlorophenyl, and 4-methoxyphenyl;
$R^{1a}$ is selected from $NH_2$, $NH(C_{1-4}$ alkyl), $N(C_{1-4}$ alkyl)$_2$, $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;
R is selected from Cl, Br, I, $C_{1-6}$ alkoxy, and $NR^1R^2$;
$R^1$ and $R^2$ are independently selected from $C_{1-6}$ alkyl, cyclopropyl, cyclobutyl, cyclopentyl, cyclohexyl, phenyl, and benzyl;
alternatively, $NR^1R^2$ is a 3-8 membered ring consisting of: carbon atoms, N, and 0-1 O atoms;
ring A is substituted with 0-1 $R^4$;
B is selected from F, Cl, Br, I, $OSO_2CF_3$, and $OSO_2Ph$-p-Me; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

In a 25$^{th}$ embodiment, the present invention provides a novel process wherein:
Z is selected from Cl, Br, and I;
ring D is selected from 3-chlorophenyl and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;
R is selected from Cl, Br, I, $C_{1-6}$ and $NR^1R^2$;
$NR^1R^2$ is selected from morpholino, pyrrolidino, and piperidino;
B is I;
ring A is substituted with 0-1 $R^4$; and
$R^4$ is selected from H and F.

In a 26$^{th}$ embodiment, the present invention provides a novel process wherein:
Z is Cl;
ring D is selected from 3-chlorophenyl and 4-methoxyphenyl;
$R^{1a}$ is selected from $CH_3$ and $OCH_2CH_3$;
R is selected from Cl and morpholino;
B is I; and
ring A is unsubstituted.

In a 27$^{th}$ embodiment, in reaction (e), the compound of formula I is contacted with the compound of formula IIb followed by the addition of the second base.

In a 28$^{th}$ embodiment, the second base in reaction (e) is a substituted amine base.

In a 29$^{th}$ embodiment, the substituted amine base is selected from: triethylamine, diisopropylethylamine, dabco, DBN, DBU, and N-methylmorpholine.

In a 30$^{th}$ embodiment, the substituted amine base is diisopropylethylamine.

In a 31$^{st}$ embodiment, in reaction (e), the contacting is performed in the presence of a fifth aprotic solvent.

In a 32$^{nd}$ embodiment, the fifth aprotic solvent is dichloroethane.

In a 33$^{rd}$ embodiment, reaction (e) further comprises contacting with a second strong acid.

In a 34$^{th}$ embodiment, the second acid is TFA.

In a 35$^{th}$ embodiment, in reaction (d) the catalyst is a Cu(I) salt or a Pd(II) salt.

In a 36$^{th}$ embodiment, in reaction (d) the catalyst is selected from CuI, CuCl, CuBr, and CuOTf.

In a 37$^{th}$ embodiment, in reaction (d), the catalyst is CuI.

In a 38$^{th}$ embodiment, in reaction (d), the fourth aprotic solvent is selected from DMSO, toluene, N-methylpyrrolidinone, DMAC, and DMF.

In a 39$^{th}$ embodiment, in reaction (d), the fourth aprotic solvent is DMF.

In a 40$^{th}$ embodiment, the present invention provides a novel process for preparing a compound of formula IV:

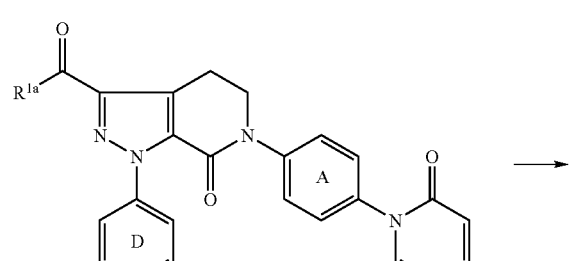

IIIc

-continued

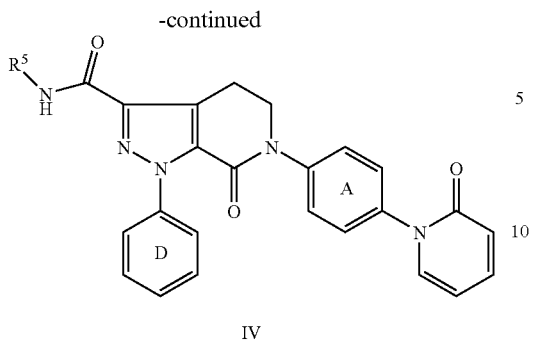

IV comprising:
(f) contacting the compound of formula IIIc with a formamide in the presence of a third base to form a compound of formula IV; wherein:
the formamide is HC(O)NHR$^5$;
the third base is an alkoxide;
ring D is selected from phenyl, 2-fluorophenyl, 3-chlorophenyl, and 4-methoxyphenyl;
R$^{1a}$ is selected from OCH$_3$, OCH$_2$CH$_3$, OCH$_2$CH$_2$CH$_3$, OCH(CH$_3$)$_2$, OCH$_2$CH$_2$CH$_2$CH$_3$, OCH(CH$_3$)CH$_2$CH$_3$, OCH$_2$CH(CH$_3$)$_2$, and OC(CH$_3$)$_3$;
ring A is substituted with 0-1 R$^4$;
B is 2-oxo-pyridyl;
R$^4$ is selected from H, OH, OCH$_3$, OCH$_2$CH$_3$, OCH$_2$CH$_2$CH$_3$, OCH(CH$_3$)$_2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, and CF$_3$; and
R$^5$ is selected from H, CH$_3$, and CH$_2$CH$_3$.

In a 41$^{st}$ embodiment, the present invention provides a novel process wherein:
ring D is selected from 3-chlorophenyl and 4-methoxyphenyl;
R$^{1a}$ is OCH$_2$CH$_3$;
ring A is substituted with 0-1 R$^4$;
R$^4$ is selected from H and F; and
R$^5$ is H.

In a 42$^{nd}$ embodiment, the present invention provides a novel process wherein:
ring D is 3-chlorophenyl;
R$^{1a}$ is OCH$_2$CH$_3$; and
ring A is unsubstituted.

In a 43$^{rd}$ embodiment, in reaction (f), the formamide is HC(O)NH$_2$; and the third base is a C$_{1-6}$ alkoxide and the counterion is selected from Li, Na, K, Li, and Mg.

In a 44$^{th}$ embodiment, in reaction (f), the third base is a sodium C$_{1-2}$ alkoxide; and an alcoholic solvent corresponding to the alkoxide is also present.

In a 45$^{th}$ embodiment, in reaction (f), the third base is NaOMe and the alcoholic solvent is methanol.

In a 46$^{th}$ embodiment, reaction (f) is conducted in the presence of a sixth aprotic solvent.

In a 47$^{th}$ embodiment, the sixth aprotic solvent is selected from DMSO, NMP, DMAC and DMF.

In a 48$^{th}$ embodiment, the sixth aprotic solvent is DMF.

In a 49$^{th}$ embodiment, the present invention provides a novel process for preparing a compound of formula IIIb:

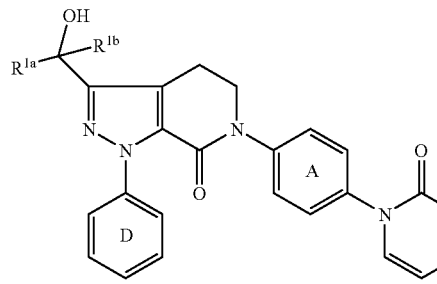

comprising:
(g) contacting a compound of formula III with an R$^{1b}$-metal reagent to form a compound of formula IIIc;

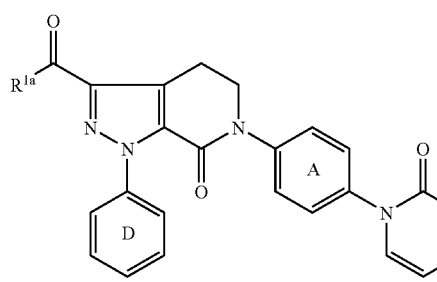

wherein:
ring D is selected from phenyl, 2-fluorophenyl, 3-chlorophenyl, and 4-methoxyphenyl;
R$^{1a}$ is selected from CH$_3$, CH$_2$CH$_3$, CH$_2$CH$_2$CH$_3$, OCH$_3$, OCH$_2$CH$_3$, OCH$_2$CH$_2$CH$_3$, OCH(CH$_3$)$_2$, OCH$_2$CH$_2$CH$_2$CH$_3$, OCH(CH$_3$)CH$_2$CH$_3$, OCH$_2$CH(CH$_3$)$_2$, and OC(CH$_3$)$_3$;
R$^{1b}$ is C$_{1-6}$ alkyl;
ring A is substituted with 0-1 R$^4$;
R$^4$ is selected from H, OH, OCH$_3$, OCH$_2$CH$_3$, OCH$_2$CH$_2$CH$_3$, OCH(CH$_3$)$_2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, and CF$_3$.

In a 50$^{th}$ embodiment, the present invention provides a novel process wherein:
ring D is selected from 3-chlorophenyl and 4-methoxyphenyl;
R$^{1a}$ is selected from CH$_3$, CH$_2$CH$_3$, and CH$_2$CH$_2$CH$_3$;
R$^{1b}$ is selected from CH$_3$ and CH$_2$CH$_3$;
ring A is substituted with 0-1 R$^4$; and
R$^4$ is selected from H and F.

In a 51$^{st}$ embodiment, the present invention provides a novel process wherein:
ring D is 4-methoxyphenyl;
R$^{1a}$ is CH$_3$;
R$^{1b}$ is CH$_3$; and
ring A is unsubstituted.

In a 52$^{nd}$ embodiment, the R$^{1b}$-metal reagent is a Grignard reagent.

In a 53$^{rd}$ embodiment, the Grignard reagent is CH$_3$MgCl.

In a 54$^{th}$ embodiment, in reaction (b), the contacting is performed in the presence of a seventh aprotic solvent.

In a 55$^{th}$ embodiment, the seventh aprotic solvent is dichloromethane.

The present invention may be embodied in other specific forms without departing from the spirit or essential attributes thereof. Thus, the above embodiments should not be considered limiting. Any and all embodiments of the present invention may be taken in conjunction with any other embodiment or embodiments to describe additional embodiments. Each individual element of the embodiments is its own independent embodiment. Furthermore, any element of an embodiment is meant to be combined with any and all other elements from any embodiment to describe an additional embodiment. In addition, the present invention encompasses combinations of different embodiment, parts of embodiments, definitions, descriptions, and examples of the invention noted herein.

Definitions

All examples provided in the definitions as well as in other portions of this application are not intended to be limiting, unless stated.

The present invention can be practiced on multigram scale, kilogram scale, multikilogram scale, or industrial scale. Multigram scale, as used herein, is can be in the scale wherein at least one starting material is present in 10 grams or more, at least 50 grams or more, or at least 100 grams or more. Multikilogram scale means the scale wherein more than one kilo of at least one starting material is used. Industrial scale means a scale which is other than a laboratory sale and which is sufficient to supply product sufficient for either clinical tests or distribution to consumers.

Equivalents mean molar equivalents unless otherwise specified.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

"Substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention includes all stable oxides of thiol and amino groups, even when not specifically written. When an amino group is listed as a substituent, the N-oxide derivative of the amino group is also included as a substituent. When a thiol group is present, the S-oxide and S,S-dioxide derivatives are also included.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

"Alkyl" includes both branched and straight-chain saturated aliphatic hydrocarbon groups having the specified number of carbon atoms. $C_{1-6}$ alkyl, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl. $C_{1-6}$ alkoxy, includes $C_1$, $C_2$, $C_3$, $C_4$, $C_5$, and $C_6$ alkoxy groups. Examples of alkoxy include methoxy, ethoxy, n-propoxy, i-propoxy, n-butoxy, s-butoxy, t-butoxy, n-pentoxy, and s-pentoxy.

The reactions of the synthetic methods claimed herein may be carried out in the presence of a suitable base, said suitable base being any of a variety of bases, the presence of which in the reaction facilitates the synthesis of the desired product. Suitable bases may be selected by one of skill in the art of organic synthesis. Suitable bases include inorganic bases such as alkyl lithium, hydrides, lithium amides, alkali metal, alkali earth metal, thallium hydroxides, and ammonium hydroxides; alkoxides; phosphates; and, carbonates such as sodium hydroxide, potassium hydroxide, sodium carbonate, potassium carbonate, cesium carbonate, thallium hydroxide, thallium carbonate, tetra-n-butylammonium carbonate, and ammonium hydroxide. Suitable bases include methyl lithium, ethyl lithium, n-propyl lithium, i-propyl lithium, n-butyl lithium, i-butyl lithium, s-butyl lithium, t-butyl lithium, hexyl lithium, lithium bis(trimethylsilyl) amide, lithium diisopropylamide, lithium 2,2,2,-tetramethylpiperidine, potassium bis(trimethylsilyl)amide, potassium hydride, or sodium hydride.

"Substituted amine base" includes a tertiary amine base. Examples include trialkylamines wherein the three alkyl groups can be the same or different. Examples of alkyl include methyl, ethyl, n-propyl, i-propyl, n-butyl, s-butyl, t-butyl, n-pentyl, and s-pentyl. The alkyl groups on the substituted amine base also include cycloakyl groups (e.g., cyclopropyl, cyclobutyl, cyclopentyl, and cyclohexyl) and cycloalkyl-alkyl groups (e.g., cyclopropyl-methyl, cyclobutyl-methyl, cyclopentyl-methyl, and cyclohexyl-methyl). Substituted amine bases can also include monocyclic, bicyclic, and tryicyclic amine bases. Examples of substituted amine bases include triimethylamine, triethylamine, tri-n-propylamine, diisopropylethylamine, dabco (1,4-diazabicyclo[2.2.2]octane), DBN (1,5-diazabicyclo[4.3.0]non-5-ene), and DBU (1,8-diazabicyclo[5.5.0]undec-7-ene).

"Strong base" or "strongly basic conditions" includes alkyl lithiums, lithium amides, hydride bases, other organometallic bases, and t-butoxides. Examples of strong bases include lithium tert-butoxide, sodium tert-butoxide, potassium tert-butoxide, methyl lithium, ethyl lithium, n-propyl lithium, i-propyl lithium, n-butyl lithium, i-butyl lithium, s-butyl lithium, t-butyl lithium, hexyl lithium, lithium bis (trimethylsilyl)amide, lithium diisopropylamide, lithium 2,2,2,-tetramethylpiperidine, potassium bis(trimethylsilyl)amide, potassium hydride, and sodium hydride.

"Strong acid" or "strongly acidic conditions" includes TFA (trifluoroacetic acid), sulfuric acid, and sulfonic acids (e.g., benzene sulfonic acid, toluene sulfonic acid, methyl sulfonic acid, and naphthalene sulfonic acid).

Suitable aprotic solvents include ether solvents, tetrahydrofuran (THF), dimethylformamide (DMF), 1,2-dimethoxyethane (DME), diethoxymethane, dimethoxymethane, dimethylacetamide (DMAC), benzene, toluene, 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

"Pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Stable compound" and "stable structure" indicate a compound that is sufficiently robust to survive isolation to a useful degree of purity from a reaction mixture, and formulation into an efficacious therapeutic agent.

"Substituted" indicates that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Synthesis

By way of example and without limitation, the present invention may be further understood by the following schemes and descriptions.

1,3-Dipolar Cycloaddition

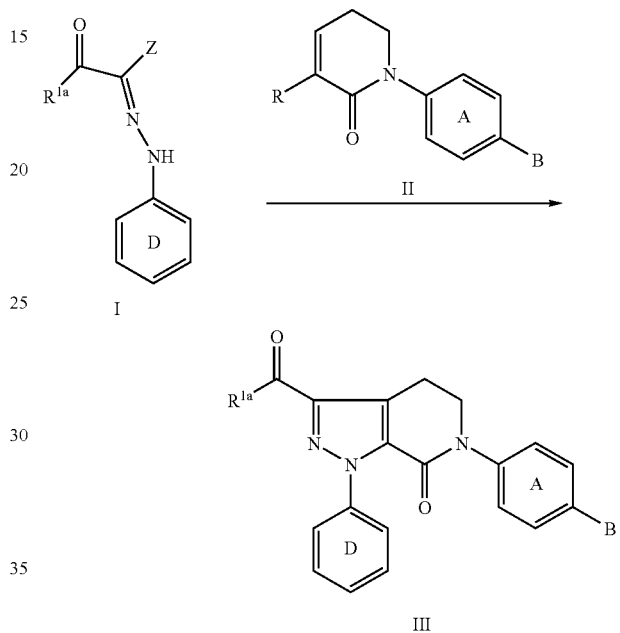

The 1,3-dipolar cycloaddition reaction of the present invention involves reaction between the hydrazonoyl compound of formula I and dipolarophile of formula II. Compounds of formula I can be prepared as described in US 2003/0181466, the contents of which are incorporated herein. This cycloaddition reaction provides the 4,5-dihydro-pyrazolo[3,4-c]pyrid-2-one cores. The reaction can be run in the presence of a substituted amine base (e.g., a non-nucleophilic tertiary amine base). Examples of substituted amine bases include (a) trialkyamines (e.g., triethylamine and diisopropylethylamine) and cyclic tertiary amines (e.g., N-methylmorpholine, dabco, DBN, or DBU), (b) trialkylamines and (c) triethylamine or diisopropylethylamine. Examples of equivalents of base used include (a) about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, to 3.5 and (b) 3. Aprotic solvents (e.g., toluene, ethyl acetate, and dichloroethane) can be for the cycloaddition. The cycloaddition can be run from room temperature up to the reflux point of the solvent. Examples of temperatures for the reaction include (a) from about 80, 85, 90, 95, to 100° C. and (b) about 90° C.

Hydrazonoyl compound I can first be contacted with the base or dipolarophile (II), followed by addition of the second component. For example, dipolarophile (II) can be contacted with hydrazonoyl compound (I) and addition of the base can then follow. Alternatively, the hydrazone (I) can be contacted with a base and addition of dipolarophile (II) can then follow.

After contacting I and II in the presence of a base, the resulting product can be contacted with a strong acid. Examples of strong acids include (a) TFA, sulfuric acid, nitric acid, and HCl and (b) TFA and HCl.

Grignard Addition

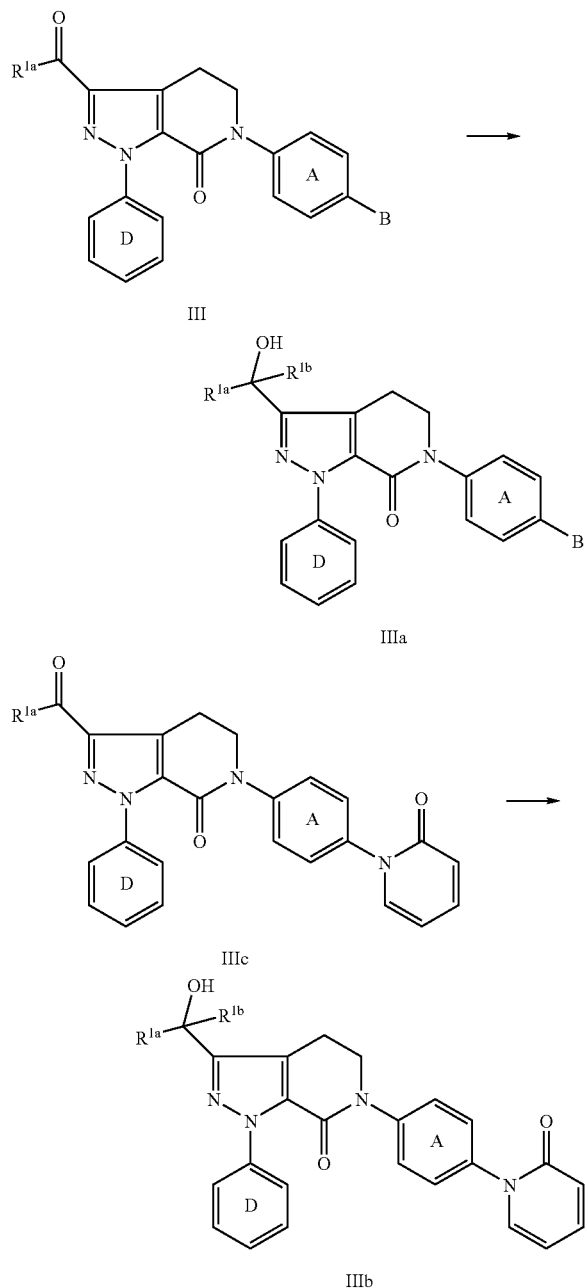

Alcohols IIIa and IIIb can be prepared from a compound of formula III (wherein $R^{1a}$ can be a $C_{1-3}$ alkyl group and B can be I) or IIIb (wherein $R^{1a}$ can be $C_{1-3}$ alkyl) via an alkyl-metal addition. The metal reagent can be one of a variety of agents known to those of skill in the art (e.g., Grignard, Li, Zn, Mg, Ce, Ti, Al, Cd). Examples of Grignard reagents include (a) MeMgBr, MeMgCl, MeMgI, and $Me_2Mg$ and (b) MeMgCl. Examples of solvents include (a) an aprotic, non-carbonyl containing solvent, (b) THF, methyl-THF, toluene, MTBE, dichloromethane, and (c) dichloromethane. Examples of temperatures for the reaction include (a) about 0, 2, 4, 6, 8, 10, 12, 14, 16, 18, 20, 22, 24, 26, 28, 30, 32, 34, 36, 38, to 40° C. and (b) 10° C.

Ullmann Coupling

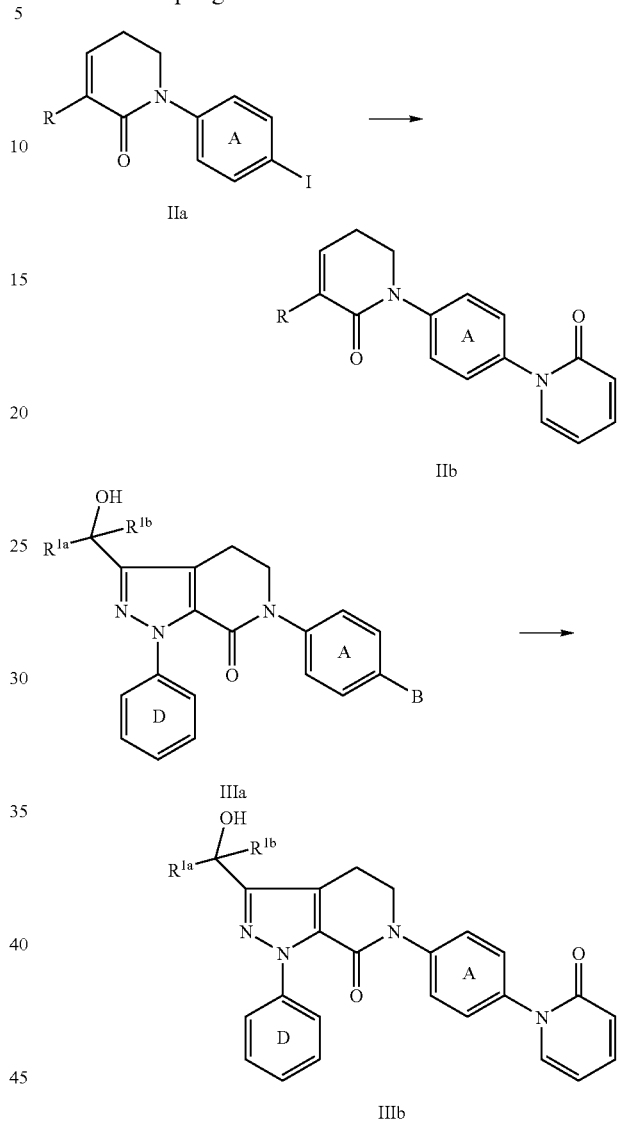

The compound of formula IIb/IIIb can be formed from formula IIa/IIIa by contacting with 2-hydroxy-pyridine in the presence of a catalyst and an aprotic solvent. Examples of catalysts include (a) Cu(I) salt or a Pd(II) salt, (b) CuI, CuCl, CuBr, CuOTf, and $Pd(OAc)_2$, and (c) CuI. The addition of 2-hydroxy-pyridine is generally aided by the presence of a base that is strong enough to deprotonate the hydroxyl group. Examples of such bases include inorganic bases (e.g., phosphates (e.g., $K_3PO_4$), carbonates (e.g., $K_2CO_3$), hydroxides (e.g., KOH), and hydrides (e.g., NaH)) and organic bases (e.g., NaHMDS, LDA, and t-butoxides (e.g., KOtBu). An example of a base for IIIb is KOtBu. An example of a base for IIb is $K_3PO_4$. The formation of IIIb can be conducted in the presence of bidentate-diamine ligands, which are known to those of ordinary skill in the art (see, for example, Klapars et al, *J. Am. Chem. Soc.* 2002, 124, 7421-28). Examples of ligands included, but are not limited to, phenanthrolines (e.g., 1,10 or 2,9), neocuproine, creatine, amino acids, 8-hydroxy-quinoline, and 2-pyridamine and (b) 1,10-phenanthroline. Examples of the aprotic solvent include (a) a high boiling point solvent (e.g., boiling point over 60° C.), (b) DMSO, toluene, N-methylpyrrolidinone, DMAC, and DMF, and (c) DMF.

Amidation

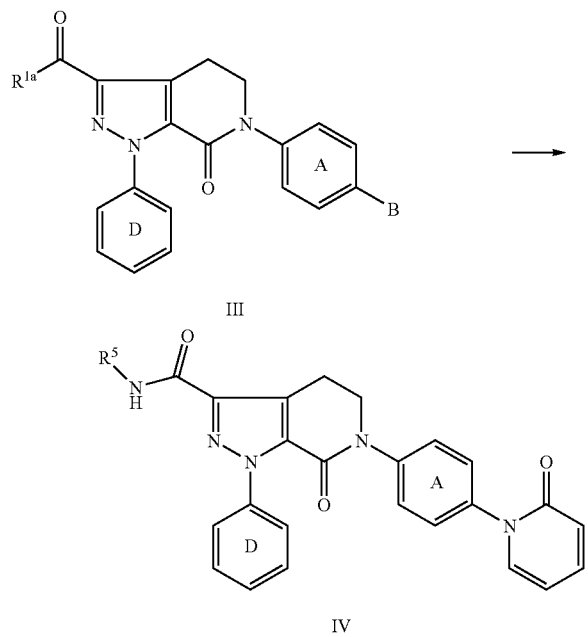

Amide IV can be formed from III (wherein $R^{1a}$ is an ester (e.g., ether ester) and B is 2-oxo-pyridyl) by contacting with a formamide and a base. Examples of formaides include (a) N-ethyl-formamide, N-methyl-formamide, or formamide and b) formamide itself. Examples of bases include (a) alkoxides, (b) $C_{1-6}$ alkoxide, and (c) methoxide. Examples of counterions for the alkoxide include (a) Li, Na, K, Li, and Mg and (b) Na. The reaction can be conducted in the presence of an alcohol that corresponds to the alkoxide base (e.g., $C_{1-6}$ alcohols and methanol). Examples of solvents for the amidation include (a) aprotic, (b) DMSO, NMP, DMAC, and DMF, and (c) DMF. Examples of reaction temperatures include (a) room temperature up to the reflux point of the solvent used and (b) room temperature to 100° C.

Other features of the invention will become apparent in the course of the following descriptions of examplary embodiments which are given for illustration of the invention and are not intended to be limiting thereof.

EXAMPLES

Example 1

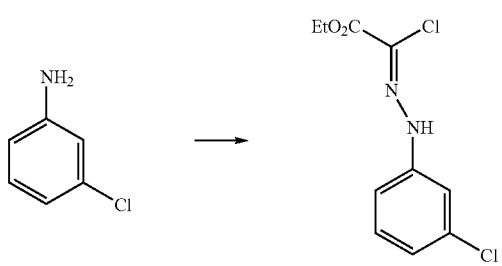

To acetic acid (102 g, 115 mL, 2.0 mol) was added water (120 g, 120 mL, 6.66 mol), liquid HCl, 12.2M in $H_2O$ (198 g, 165 mL, 2.01 mol), water (100 g, 100 mL, 5.55 mol), and then m-chloroaniline (128 g, 105 mL, 1.0 mol) while maintaining the temperature at 20-30° C. This solution was then cooled to −5 to 0° C. and to it was added sodium nitrite (76.0 g, 1.10 mol) and then water (150 g, 150 mL, 8.33 mol). To this solution was added sodium acetate trihydrate (272 g, 2.00 mol), followed by water (500 g, 500 mL, 27.8 mol). Toluene (218 g, 250 mL, 2.36 mol, ethyl 2-chloro-3-oxo butanoic acid (165 g, 138 mL, 1.00 mol), and toluene (43.6 g, 50 mL, 473 mmol) were then sequentially added while maintaining the temperature at −5 to 0° C. After maintaining the temperature at −5 to 0° C. for 30 minutes, the solution was heated to 50-55° C. the reaction was complete and then cooled to 30-35° C. The organic (heavy) phase was removed. To the aqueous phase was added toluene (34.8 g, 40 mL, 378 mmol) and heptane (246 g, 360 mL, 2.46 mol). This solution was heated to 40-55° C., and heptane (1.03 kg, 1.50 L, 10.2 mol) was added over 1 hour. Once crystallization started, additional heptane was added (684 g, 1.00 L, 6.83 mol) over 1 hour. The solution was cooled to −5 to 0° C. over two hours and held at this temperature for 2 hours. The precipitate was filtered and dried to provide the desired product (200 g, 766 mmol, 0.766 equiv.).

Example 2

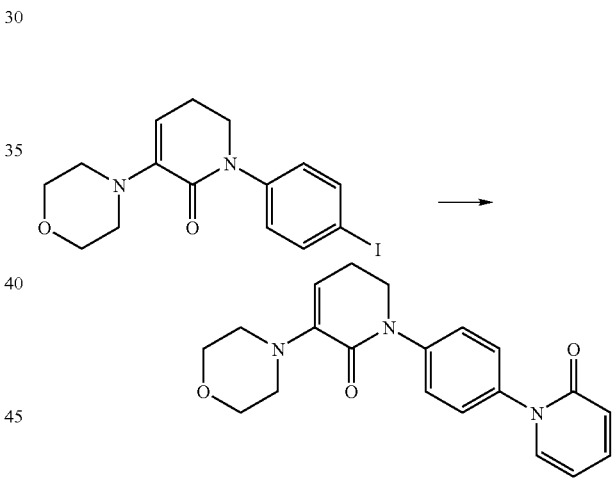

To 1-(4-iodo-phenyl)-3-morpholin-4-yl-5,6-dihydro-1H-pyridin-2-one (100 g, 260 mmol)(see Example 8 of US 2003/0181466), under a nitrogen atmosphere, were added 2-hydroxypyridine (37.1 g, 390 mmol), tribasic potassium phosphate N-hydrate (82.8 g, 390 mmol), Cu(I) I (9.90 g, 52.0 mmol), and DMF (535 g, 520 mL). While maintaining the nitrogen atmosphere, the solution was heated to 30-40° C. for about 15 minutes and then to 120-125° C. until the reaction was over 90% complete. The solution was cooled to about 30-40° C. and ammonium hydroxide 28 wt/wt % in water (156 g, 173 mL) was added. Water (347 g, 347 mL) was added while maintaining the temperature at 20-30° C. Ammonium hydroxide solution (10%) was added while the reaction mixture was at 30-40° C. The solution was cooled to 20-25° C. and agitated for about 1 hour. The precipitate was filtered and washed with water (520 g, 520 mL)(twice)

and methyl t-butyl ether (742 g, 520 mL), and then dried to yield the desired product (68.6-72.2 g, 0.195-0.205 mol, 0.75-0.79 equiv.).

Example 3

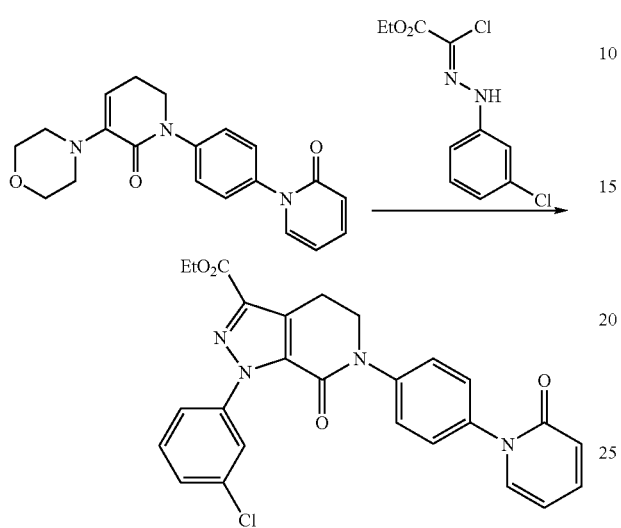

To the products from Example 2 (50 g, 142.29 mmol, 1.00 equiv.) and from Example 1 (74.30 g, 284.58 mmol, 2.00 equiv.) were added 1,2-dichloroethane (499.20 g, 400 mL, 5.04 mol) and diisopropylethylamine (55.17 g, 74.44 mL, 425.86 mmol). The reaction mixture was heated to 77° C. and stirred for 16 h to achieve a 90% conversion. After cooling to 40° C., TFA (64.90 g, 43.04 mL, 569.15 mmol) was added dropwise, and the solution was heated to 80° C. for 1 hour. After cooling to 25° C., water (400 g, 400 mL, 22.2 mol) was added and the bottom phase collected. Ethanol (124.80, 100 mL, 1.26 mol) was added, and the solution was reduced by about 275 mL by distillation. After cooling to 5° C., ethanol (197.82 g, 250 mL, 4.29 mol) was added. Another 334 mL of the resulting solution were distilled off. Ethanol (197.82, 250 mL, 4.29 mol) was slowly added after cooling to 65° C. The solution was then cooled to 4° C. over 2 h. The resulting precipitate was filtered, washed with acetone (395.05 g, 500 mL, 6.80 mol) and dried to yield the desired product (49 g, 70.4% yield).

Example 4

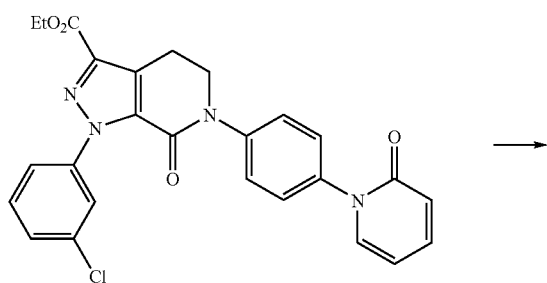

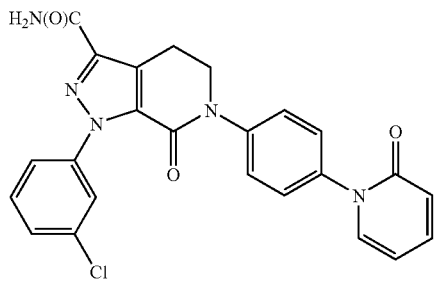

Example 3 (1 kg, 2.05 mol, 1 equiv.) and DMF (9.45 kg, 10.0 L) were stirred at about 25° C. Formamide (2.26 kg, 2.0 L) was added and the solution was heated to 50-55° C. over a period of about 10 min. After about 10 min, 25 wt % sodium methoxide (0.4641 kg, 0.4937 L, 2.148 mol, 1.05 equiv.) was added while the temperature was maintained at 50-55° C. After 15 minutes, 28 wt % ammonium hydroxide (2.56 kg, 2.85 L, 42.4 mol, 20.7 equiv.) was added over 1 h. The reaction solution was cooled to about 20° C. over about 1 h. The resulting precipitate was filtered, washed with water (10 kg, 10 L) (twice) and acetone (10 L) and dried.

Example 5

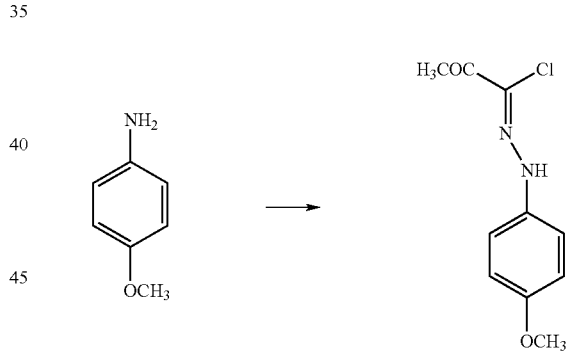

P-anisidine (7.4 kg) was dissolved in water (18.6 l) and hydrochloric acid (33% HCl, 18 L) was added. The solution was heated to 40° C. and stirred for 30 minutes. The reaction mixture was then cooled to −5° C., and an aqueous sodium nitrite (8 L at 40% w/w) solution was added. Afterwards, the reaction mixture was stirred for another 30 minutes at about 0° C. The prepared solution was slowly dosed at −5° C. to a solution of aqueous sodium acetate (9.8 kg of NaOAc in 24 L of water), 3-chloro-2,4-pentandione (8.17 kg), and acetone (18 L). The resulting mixture was stirred for 1 hour. The reaction mixture was then brought to 25° C. over a 6 hour period. A slurry was formed. The precipitate was filtered and washed once with water. The isolated solid was dried under vacuum to obtain 12.2 kg of the desired product.

Example 6

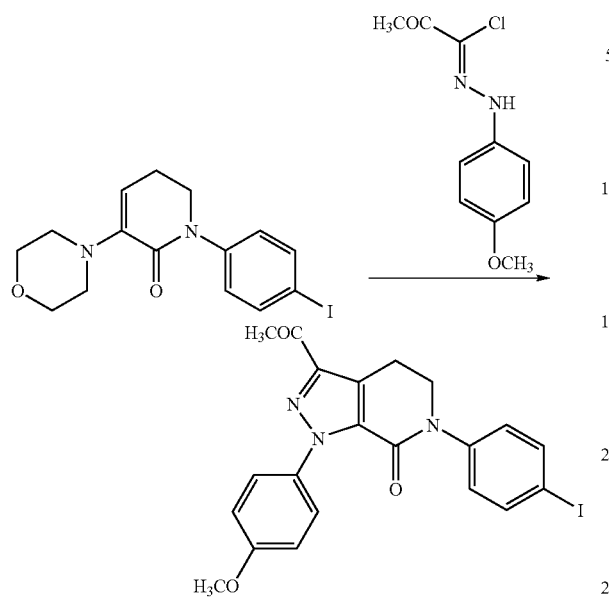

The products from Example 5 (4 kg, a second 3.9 kg batch was also run) and 1-(4-iodo-phenyl)-3-morpholin-4-yl-5,6-dihydro-1H-pyridin-2-one (4.5 kg) were suspended in ethyl acetate (20 L), then triethylamine (2.45 l) was added. The transfer lines were rinse with 3.4 L of ethyl acetate. The resulting suspension was heated to 70° C. and stirred for about 4 hours. Next, the solution was diluted with ethyl acetate (35 L) and water (23.4 L). After cooling to 25° C., the solution was subjected to a polish-filtration to eliminate the fine particles. After phase separation, the aqueous phase was extracted with ethyl acetate (10.2 L). HCl (33% HCl, 2.35 L) was added to the combined organic layers, and the mixture was heated to 5° C. for 90 minutes. After cooling to room temperature, water (20.5 L) was added. After phase separation, the organic layer was extracted with sodium carbonate solution (34 L at 2.6 w/w) and then water 34 L and 0.6 L of methanol. The resulting product solution was reduced to 30% of the volume and petrol ether (47.5 L) was added. The rest of the ethyl acetate was removed by distillation. Methanol (9.5 L) was added, and the solution was brought to reflux for at about 10 minutes. While cooling, the product started to crystallize. The suspension was stirred for 1 hour at 20° C., and then the solid product was filtered off. The wet isolated product from the two batches were combined and dried to obtain 6.86 kg of desired product.

Example 7

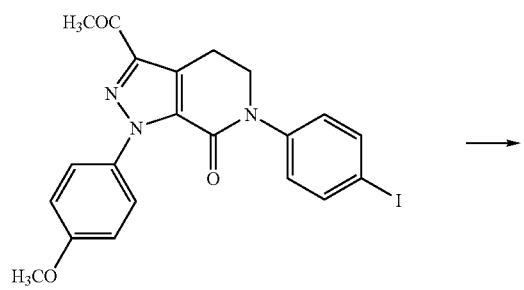

The product from Example 6 (2.5 kg, two batches of 2.5 kg were run) was dissolved in methylene chloride (58 L) and reacted with a solution of methylmagnesium chloride in THF (3.45 kg, 3M) at 10° C. over 2 hours. The reaction was monitored by HPLC. Once the end-point was reached, the reaction mixture was transferred to another vessel with a 10 L rinse of DCM (dichloromethane), and the reaction was quenched with an aqueous solution of ammonium chloride (23.3 L, 12% w/w) at a temperature below 20° C. After phase separation, the organic layer was washed with ammonium chloride solution (23.3 L at 12% w/w) and then with water (236 kg). Acetone (50 l) and toluene (23.6 l) was added, and a solvent swap was performed by distilling off the methylene chloride. The resulting slurry was cooled to 5° C., and the product was filtered off and washed with toluene (7.1 L) and heptane (7.1 L). The wet isolated product from the two batches were combined to obtain 3 kg of the desired product).

Example 8

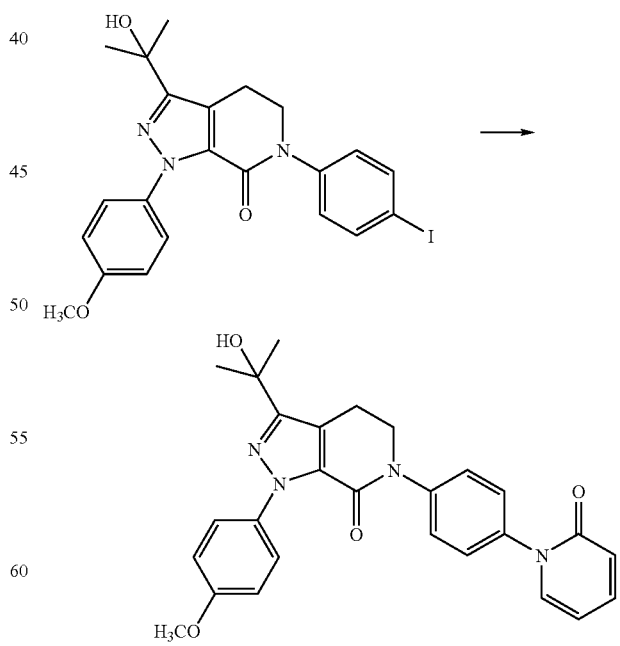

Under a nitrogen atmosphere, the product from Example 7 (3 kg), CuI (0.136 kg), 1,10-phenanthroline (0.214 kg), potassium tert-butoxide (1 kg), and 2-hydroxypyridine (0.850 kg) were suspended in DMF (13.8 L). The DMF solvent was sparged with nitrogen before charging the reagents to minimize the dissolved oxygen. The reaction mixture was heated to 125° C. for 23 hours. The end-point was determined by HPLC. Once the end-point had been reached, the reaction mixture was cooled to about 25° C., and solid potassium phosphate (1.26 kg) powder was added. After 45 minutes of stirring, ammonium hydroxide solution (15 l at 10% w/w) was added slowly and stirring was extended for 30 minutes while the product crystallized out. The resulting slurry was then filtered and washed successively with ammonium hydroxide (15 l, 10% w/w), water (three times with 15 l), and MTBE (15 l). The isolated final product was dried at 50-60° C. under vacuum to obtain 2.12 kg.

Example 9

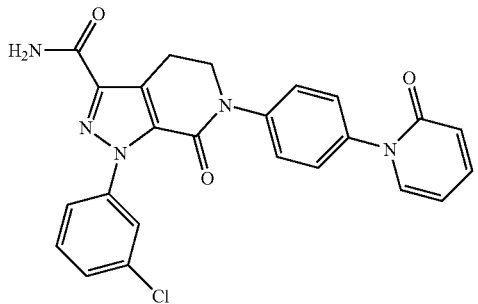

A 5 L 3-neck round bottom flask was charged with Example 3 (100 g, 204 mmol), DMF (800 mL), HCONH$_2$ (180 mL), and sodium methoxide (25 g, 252 mmol). After the reaction mixture was stirred at 65° C. under N$_2$ for 1 hour, aq. NH$_4$OH (800 mL 1N) was added over 30 minutes. The solid was collected by filtration and washed with H$_2$O (3×500 mL). The white solid was dried in vacuo at 50° C. for 16 hour to provide the product (91.0 g, 96.8%) as white solid. $^1$H NMR (DMSO): δ 7.79 (d, J=13.8 Hz, 2H); 7.63(d, J=7.2 Hz, 2H); 7.50 (m, 5H); 7.41 (d, J=8.2 Hz, 3H); 6.47 (d, J=9.3 Hz, 1H); 6.30 (t, J=6.5 Hz, 1H); 4.10 (t, J=6.1 Hz, 2H); 3.22 (t, J=6.0 Hz, 2H), 1.46 (t, J=7.1 Hz, 3H). $^{13}$C NMR (DMSO): δ 162.8, 161.0, 156.4, 142.2, 141.5, 140.4, 140.2, 138.8, 138.2, 133.1, 132.4, 129.8, 128.1, 126.8, 126.1, 125.9, 125.1, 124.0, 120.4, 105.5, 50.7, 20.9.

Example 10

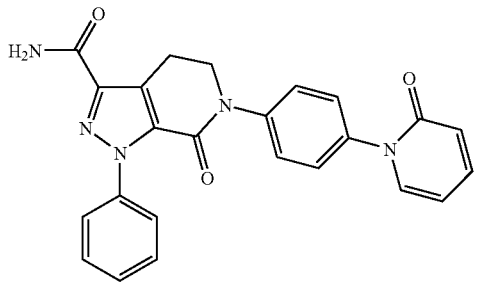

7-Oxo-6-(4-(2-oxopyridin-1(2H)-yl)phenyl)-1-phenyl-4,5,6,7-tetrahydro-1H-pyrazolo[3,4-c]pyridine-3-carboxamide was prepared similarly to Example 9.

Example 11

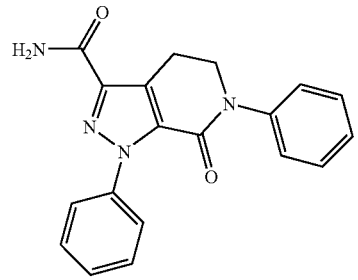

7-Oxo-1,6-diphenyl-4,5,6,7-tetrahydro-1H-pyrazolo[3,4-c]pyridine-3-carboxamide was prepared similarly to Example 9.

Example 12

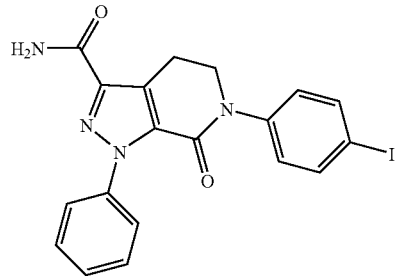

6-(4-Iodophenyl)-7-oxo-1-phenyl-4,5,6,7-tetrahydro-1H-pyrazolo[3,4-c]pyridine-3-carboxamide was prepared similarly to Example 9.

Example 13

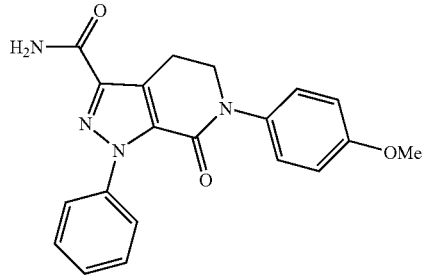

6-(4-Methoxyphenyl)-7-oxo-1-phenyl-4,5,6,7-tetrahydro-1H-pyrazolo[3,4-c]pyridine-3-carboxamide was prepared similarly to Example 9.

Example 14

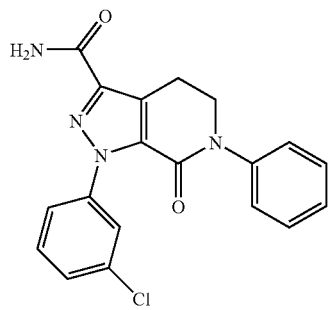

1-(3-Chlorophenyl)-7-oxo-6-phenyl-4,5,6,7-tetrahydro-1H-pyrazolo[3,4-c]pyridine-3-carboxamide was prepared similarly to Example 9.

Example 15

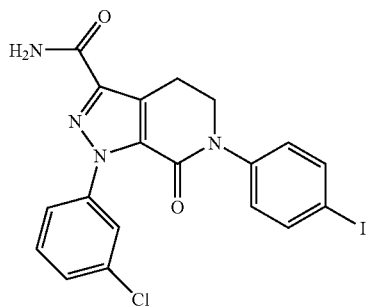

1-(3-Chlorophenyl)-6-(4-iodophenyl)-7-oxo-4,5,6,7-tetrahydro-1H-pyrazolo[3,4-c]pyridine-3-carboxamide was prepared similarly to Example 9.

Example 16

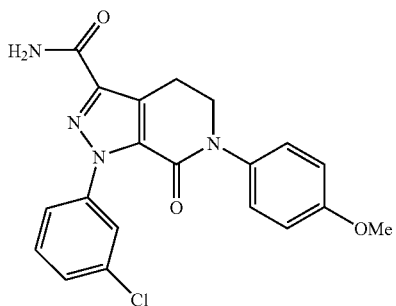

1-(3-Chlorophenyl)-6-(4-methoxyphenyl)-7-oxo-4,5,6,7-tetrahydro-1H-pyrazolo[3,4-c]pyridine-3-carboxamide was prepared similarly to Example 9.

Example 17

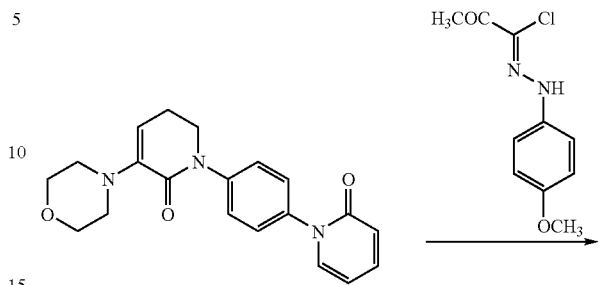

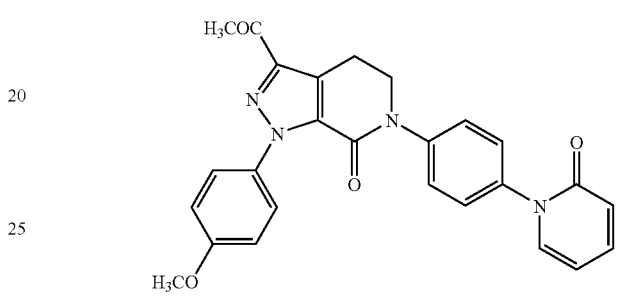

To the products from Example 2 (10.00 g, 28.46 mmol, 1.00 equiv.) and from Example 5 (13.44 g, 42.69 mmol, 1.50 equiv.) were added 1,2-dichloroethane (112.32 g, 90 mL, 1.14 mol) and diisopropylethylamine (5.52 g, 7.44 mL, 42.69 mmol). The reaction mixture was heated to 80° C., stirred for 24 h, cooled to 72° C., TFA (7.14 g, 4.73 mL, 62.61 mmol) was added dropwise, and then the solution was stirred for 1 h. After cooling to 40° C., water (80.0 g, 80.0 mL, 4.44 mol) was added and the bottom phase collected and washed with water (80.0 g, 80.0 mL, 4.44 mol). Ethanol (126.61 g, 160 mL, 2.75 mol) was added, and the solution was reduced by about 90 mL by distillation. After cooling to 5o° C., ethanol (63 g, 80 mL, 1.4 mol) was added. The solution was then cooled to room temperature. The resulting precipitate was filtered, washed with ethanol (3×80 mL), and dried to yield the desired product (9.3 g, 72% yield).

Example 18

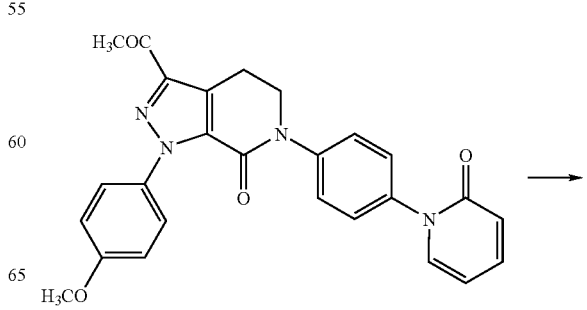

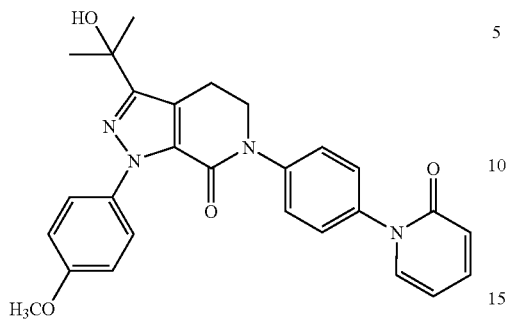

The product from Example 17 (2.00 g, 4.40 mmol, 1.00 equiv.) was dissolved in dichloromethane (79.50 g, 60.00 mL, 936.04 mmol), and cooled to 1.2° C. A solution of methylmagnesium chloride in THF (3 M, 2.22 g, 2.20 mL, 6.60 mmol) was then added, and the solution was allowed to warm to 5° C. After about 1.5 hours, additional methylmagnesium chloride (0.25 mL) was added, and the solution was warmed to 8° C. The reaction was quenched with an aqueous solution of ammonium chloride (30 mL, 12% w/w), and the solution was allowed to rise to room temperature. After phase separation, to the organic layer was added ethanol (60 mL). About 100 mL of the solution was then distilled off. The solution was cooled to 65° C. and stirred for about an hour before cooling to room temperature. The resulting product was filtered off and washed with ethanol (10 mL) and dried to give 1.63 g (78.8%) of the desired product).

Numerous modifications and variations of the present invention are possible in light of the above teachings. It is therefore to be understood that within the scope of the appended claims, the invention may be practiced otherwise than as specifically described herein.

What is claimed is:

1. A process for preparing a compound of formula IIIa:

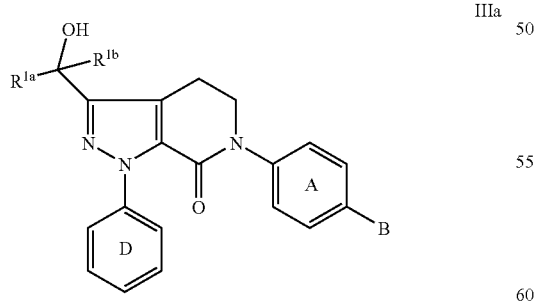

comprising:
(a) contacting a compound of formula I with a compound of formula II in the presence of a first base to form a compound of formula III;

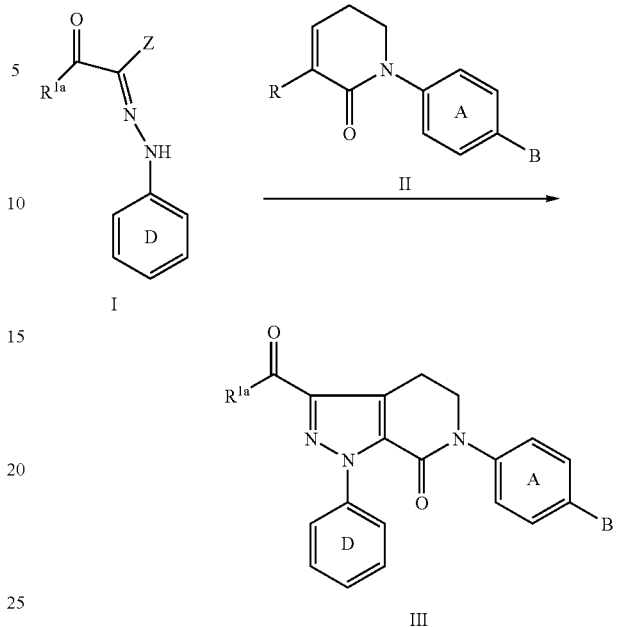

(b) contacting a compound of formula III with an $R^{1b}$-metal reagent to form a compound of formula IIIa;

wherein:
Z is selected from Cl, Br, I, $OSO_2CF_3$, $OSO_2Me$, $OSO_2Ph$, and $OSO_2Ph$-p-Me;

ring D is selected from phenyl, 2-fluorophenyl, 3-chlorophenyl, and 4-methoxyphenyl;

$R^{1a}$ is selected from $CH_3$, $CH_2CH_3$, and $CH_2CH_2CH_3$;

$R^{1b}$ is $C_{1-6}$ alkyl;

R is selected from Cl, Br, I, $C_{1-6}$ alkoxy, and $NR^1R^2$;

$R^1$ and $R^2$ are independently selected from $C_{1-6}$ alkyl, cyclopropyl, cyclobutyl, cyclopentyl, cyclohexyl, phenyl, and benzyl;

alternatively, $NR^1R^2$ is a 3-8 membered ring consisting of: carbon atoms, N, and 0-1 O atoms;

ring A is substituted with 0-1 $R^4$ in addition to B;

B is selected from F, Cl, Br, I, $OSO_2CF_3$, $OSO_2Ph$-p-Me, and 2-oxo-pyridyl; and $R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

2. A process according to claim 1, wherein:
Z is selected from Cl, Br, and I;

ring D is selected from 3-chlorophenyl and 4-methoxyphenyl;

$R^{1a}$ is selected from $CH_3$, $CH_2CH_3$, and $CH_2CH_2CH_3$;

$R^{1b}$ is selected from $CH_3$ and $CH_2CH_3$;

R is selected from Cl, Br, I, and $NR^1R^2$;

$NR^1R^2$ is selected from morpholino, pyrrolidino, and piperidino;

ring A is substituted with 0-1 $R^4$ in addition to B; and $R^4$ is selected from H and F.

3. A process according to claim 2, wherein:
Z is Cl;
ring D is 4-methoxyphenyl;
$R^{1a}$ is $CH_3$;
$R^{1b}$ is $CH_3$;
R is morpholino; and
ring A is substituted with only B.

4. A process according to claim 1, wherein: in reaction (a), the compound of formula I is contacted with the compound of formula II followed by the addition of the first base.

5. A process according to claim 1, wherein: the first base in reaction (a) is a substituted amine base.

6. A process according to claim 5, wherein: the substituted amine base is selected from: triethylamine, diisopropylethylamine, dabco, DBN, DBU, and N-methylmorpholine.

7. A process according to claim 6, wherein: the substituted amine base is triethylamine.

8. A process according to claim 1, wherein: in reaction (a), the contacting is performed in the presence of a first aprotic solvent.

9. A process according to claim 8, wherein: the first aprotic solvent is ethyl acetate.

10. A process according to claim 1, wherein: reaction (a) further comprises contacting with a first strong acid.

11. A process according to claim 10, wherein: the first acid is HCl.

12. A process according to claim 1, wherein: the $R^{1b}$-metal reagent is a Grignard reagent.

13. A process according to claim 12, wherein: the Grignard reagent is $CH_3MgCl$.

14. A process according to claim 1, wherein: in reaction (b), the contacting is performed in the presence of a second aprotic solvent.

15. A process according to claim 14, wherein: the second aprotic solvent is methylene chloride.

* * * * *